US007488865B2

(12) United States Patent
Lee et al.

(10) Patent No.: US 7,488,865 B2
(45) Date of Patent: Feb. 10, 2009

(54) UROCORTIN-DEFICIENT MICE AND USES THEREOF

(75) Inventors: Kuo-Fen Lee, Del Mar, CA (US); Wylie Vale, La Jolla, CA (US); Chien Li, San Diego, CA (US); Lingyun Zhao, San Diego, CA (US); Douglas E. Vetter, Boston, MA (US)

(73) Assignee: Research Development Foundation, Carson City, NV (US)

( * ) Notice: Subject to any disclaimer, the term of this patent is extended or adjusted under 35 U.S.C. 154(b) by 971 days.

(21) Appl. No.: 10/440,636

(22) Filed: May 19, 2003

(65) Prior Publication Data

US 2004/0055028 A1 Mar. 18, 2004

Related U.S. Application Data

(60) Provisional application No. 60/381,936, filed on May 20, 2002, now abandoned.

(51) Int. Cl.
*A01K 67/00* (2006.01)
*A01K 67/027* (2006.01)
*A01K 67/033* (2006.01)

(52) U.S. Cl. .......................................... 800/18; 800/13
(58) Field of Classification Search .................... 800/18
See application file for complete search history.

(56) References Cited

U.S. PATENT DOCUMENTS 6,147,275 A 11/2000 Vale et al. ...................... 800/18
6,353,152 B1 3/2002 Lee et al. ...................... 800/18

OTHER PUBLICATIONS

Doetschman, T. (1999) Interpretation of phenotype in genetically engineered mice. Laboratory Animal Science 49(2): 137-143.*
Donehower et al. (1995) Effects of genetic background on tumorigenesis in p53-deficient mice. Molecular Carcinogenesis 14: 16-22.*
Jacks et al. (1992) Effects of an Rb mutation in the mouse. Nature 359: 295-300.*
Jaenisch et al. (1988) Transgenic Animals. Science 240: 1468-1474.*
Kuehn et al. (1987) A potential animal model for Lesch-Nyhan syndrome through introduction of HPRT mutations into mice. Nature 326: 295-298.*
Moens et al. (1993) Defects in heart and lung development in compound heterozygotes for two different targeted mutations at the N-myc locus. Development 119: 485-499.*
Petridou et al. (2003) Heterogeneous inducible mammary-specific expression of JAB/SOCS1 in lactating transgenic mice is associated with no obvious phenotype, even at the cellular level. Transgenic Research 12: 693-706.*
Sigmund, CD (2000) Viewpoint: Are studies in genetically altered mice out of control? Arterioscler. Thromb. Vasc. Biol. 20: 1425-1429.*
Wang et al. (Sep. 2002) Urocortin-deficient mice display normal stress-induced anxiety behavior and autonomic control but an impaired acoustic startle response. Molecular and Cellular Biology 22(18): 6605-6610.*
JAX Mice Price List (Jun. 1997) F1 Hybrids, p. 22.*
Bale et al., "Mice deficient for corticotropin-releasing hormone receptor-2 display anxiety-like behaviour and are hypersensitive to stress," *Nat. Genet.*, 24:410-414, 2000.
Bale et al., "Mice deficient for both corticotropin-releasing factor receptor 1 (CRFR1) and CRFR2 have an impaired stress response and display sexually dichotomous anxiety-like behavior," *J. Neurosci.*, 22:193-199, 2002.
Coste et al., "Abnormal adaptations to stress and impaired cardiovascular function in mice lacking corticotropin-releasing hormone receptor-2," *Nat. Genet.*, 24:403-409, 2000.
Cullen et al., "Urocortin, corticotropin releasing factor-2 receptors and energy balance," *Endocrinology*, 142:992-999, 2001.
Kishimoto et al., "Deletion of crhr2 reveals an anxiolytic role for corticotropin-releasing hormone receptor-2," *Nat. Genet.*, 24:415-419, 2000.
Kihara et al., "Effects of central and peripheral urocortin on fed and fasted gastroduodenal motor activity in conscious rats," *Am J Physiol Gastrointest Liver Physiol.*, 280:G406-G419, 2001.
Moreau et al., "Urocortin, a novel neuropeptide with anxiogenic-like properties," *Neuroreport*, 8:1697-1701, 1997.
Perrin et al., "Comparison of an agonist, urocortin, and an antagonist, astressin, as radioligands for characterization of corticotropin-releasing factor receptors," *J. Pharacol. Exp. Therapeutics*, 288:729-734, 1999.
Schilling et al., "Characterization of the relaxant action of urocortin, a new peptide related to corticotropin-releasing factor in the rat isolated basilar artery," *Brit. J. Pharamol.*, 125:1164-1171, 1998.
Slawecki, et al., "Neurophysiological effects of intracerebroventricular administration of urocortin," *Peptides*, 20:211-218, 1999.
Smagin et al., "The role of CRF2 receptors in corticotropin-releasing factor- and urocortin- induced anorexia," *Neuroreport*, 9:1601-1606, 1998.
Smith et al., "Corticotropin releasing factor receptor 1-deficient mice display decreased anxiety, impaired stress response, and aberrant neuroendocrine development," *Neuron*, 20(6):1093-1102.
Spina et al., "Appetite-suppressing effects of urocortin, a CRF-related neuropeptide," *Science*, 273:1561-1564, 1996.
Weninger et al., "Urocortin expression in the Edinger-Westphal nucleus is up-regulated by stress and corticotropin-releasing hormone deficiency," *Endocrinology*, 141:256-263, 2000.
Smith et al., "Corticotropin releasing factor receptor 1-deficient mice display decreased anxiety, impaired stress response, and aberrant neuroendocrine development," *Neuron*, 20(6):1093-1102, 1998.

* cited by examiner

*Primary Examiner*—Anne-Marie Falk
(74) *Attorney, Agent, or Firm*—Fulbright & Jaworski L.L.P.

(57) ABSTRACT

The present invention provides transgenic mice deficient in urocortin. Urocortin null mutant mice are hypersensitive to stress and display heightened anxiety-like behaviors in the elevated plus maze and open field tests. These mice also demonstrate physiological alterations in auditory thresholds and distortion product otoacoustic emissions. These results indicate that urocortin plays a modulatory role in anxiety-related behaviors and in contributing to the establishment of auditory thresholds. Such urocortin deficient mutant mice can provide useful models in the study of anxiety pathology and hearing physiology at the biochemical and molecular levels.

4 Claims, 10 Drawing Sheets

UROCORTIN-DEFICIENT MICE AND USES THEREOF

CROSS-REFERENCE TO RELATED APPLICATION

This non-provisional application claims benefit of provisional U.S. Ser. No. 60/381,936, filed May 20, 2002, now abandoned.

FEDERAL FUNDING LEGEND

This invention was produced in part using funds from the Federal government under grant no. NIH DK26741. Accordingly, the Federal government has certain rights in this invention.

BACKGROUND OF THE INVENTION

1. Field of the Invention

The present invention relates generally to the fields of neurobiology, endocrinology, and psychiatry. More specifically, the present invention relates to the study of anxiety and auditory function in mice deficient for the urocortin gene.

2. Description of the Related Art

Neuropeptides are ubiquitous throughout the central and peripheral nervous systems, and play both primary transmitter and modulatory roles in biology. In the nervous system, neuropeptides play important roles in nociception, feeding behavior and stress response.

A series of peptides known as the urocortin (Ucn) peptides, including urocortin, urocortin II, and urocortin III (6-8) or as stresscopin and stresscopin-related peptide (9) have been cloned. Urocortin is very similar in structure to corticotropin releasing factor (CRF), first identified from the mammalian brain (1), which has been shown to be important in regulating the hypothalamic-pituitary-adrenal (HPA) axis and to play a prominent role in stress related responses (2). Various other non-mammalian peptides, also structurally similar to CRF have also been cloned (3-5), including fish urotensin I, and amphibian sauvagine. Additionally, urocortins, like CRF, exert their bioactivities via activating CRF receptors 1 and 2 (CRF1 and CRF2) (6), but urocortin has an approximately 40 fold higher affinity for CRFR2 and about 6 fold higher affinity for CRFR1 than CRF (6). Therefore, it has been postulated that urocortin may be an endogenous ligand for CRFR2.

A complete understanding of the full role for the urocortins has remained elusive while the roles for CRF are relatively well known. An examination of urocortin expression patterns and the administration of urocortin peptides into animals followed by the measurement of physiological responses gave insight into the role of urocortin in stress related response behaviors. High expression of urocortin is found in the Edinger-Westphal nucleus, the lateral superior olive (LSO), and the supraoptic nuclei (10). Urocortin neuronal fibers are found throughout the brain including the lateral septum in the forebrain, several motor nuclei in the brainstem, the olivocochlear fiber pathway, and in the spinal cord (10).

Central administration of urocortin has been shown to induce a variety of effects including suppression of food intake (11) and modulation of gastric motility (12). As CRFR2 is localized to the ventral medial hypothalamus, a central site of food intake regulation and satiety, it is possible that urocortin acts on these receptors to affect feeding.

A central injection of urocortin can also induce behavioral consequences such as increased locomotion and anxiety (13, 14), suggesting that urocortin, similar to CRF, is an anxiogenic agent in the brain. However, since urocortin can bind and activate both CRF receptor subtypes, administered urocortin might non-selectively activate receptors in areas where endogenous urocortin may not be present.

Urocortin has also been indicated in auditory physiology. The central nervous system exerts unique control over the auditory system that is not found in any other mammalian sensory system. By means of descending efferent fibers, cell bodies located in the superior olivary complex synapse directly with the hair cells of the organ of Corti, as well as with spiral ganglion cell dendrites located immediately adjacent to the inner hair cells. The classical anatomy of the olivocochlear system has been understood for many years (15).

In general, there are two main divisions of the olivocochlear system, identified as the lateral and the medial olivocochlear system. In rodents, the lateral system may be broken down into two systems itself, namely, those cells that lie within the boundaries of the lateral superior olive, and those that lie along its margins(16). The medial olivocochlear system synapses directly with the outer hair cells, while the lateral system synapses almost exclusively with elements within the inner hair cell region, including the inner hair cells themselves (17, 18) ) and the radial dendrites of the spiral ganglion neurons(18). Such direct innervation to inner hair cells is abundant in the developing cochlea but relatively scant in adults.

There is some immunocytochemical evidence that the lateral olivocochlear system also synapses with the outer hair cells (19). Immunocytochemical data indicate that the medial olivocochlear system is purely cholinergic (19). However, the lateral olivocochlear system is neurochemically heterogeneous, and the expression of classical neurotransmitters such as gamma aminobutyric acid (GABA) and acetylcholine (ACh) is spatially segregated within the LSO(19). Cholinergic lateral olivocochlear neurons also express a number of peptides that have been proposed to act as neuromodulators (19-24). Despite the numerous peptides expressed in the olivocochlear system, the roles they play in hearing has remained unclear, although roles for calcitonin gen-related peptide (CGRP) at the cellular level have been demonstrated in amphibian lateral line (25-27).

The prior art is lacking in information regarding the physiological roles of urocortin in auditory function and stress-related behaviors and also in null mutant mice deficient for urocortin to study such roles. The present invention fulfills this longstanding need and desire in the art.

SUMMARY OF THE INVENTION

The present invention characterized the expression of urocortin and CRFR1 and CRFR2 in the neurons and their axons that constitute the olivocochlear system and examined the organ of Corti for urocortin expressing terminals. The expression of urocortin, as well as the expression localization of various CRF receptors within the organ of Corti, was localized. This is the first report of a CRF-like system within the inner ear.

To better discern the developmental and physiological roles of urocortin, urocortin null mutant mice were generated and their behavior analyzed. Mice carrying a urocortin gene null mutation exhibit heightened anxiety-like behavior in the elevated plus maze and open field tests. In addition, these urocortin deficient mice demonstrate physiological alterations in hearing thresholds and distortion products. Thus, urocortin null mutant mice provide valuable models for delineating the underlying molecular mechanisms modulating anxiety and auditory function. Study of the urocortin expression and its role in anxiety and auditory function may provide the necessary clues required for the effective management and treatment of these conditions.

The present invention is directed to a non-natural transgenic mouse with a disruption in at least one allele of the urocortin (Ucn) gene, such that said mouse does not express the urocortin protein from said allele. Preferably, the DNA sequences encoding the entire urocortin protein have been deleted. In the transgenic mouse, these DNA sequences are replaced with a neomycin resistance gene cassette. The transgenic mouse may be either heterozygous or homozygous for this replacement. Also included in an embodiment of the present invention are the progeny of a mating between a mouse of the present invention and a mouse of another strain.

Another embodiment of the present invention is the application of a urocortin-deficient mouse to the study of anxiety and to test the effects of various compounds on anxiety. For example, a method is provided of screening a compound for anxiety-modulating activity, comprising the steps of: a) administering the compound to the transgenic mouse of the present invention; b) testing the mouse for anxiety-related behavior; and c) comparing anxiety-like behavior of the mouse with anxiety-like behavior in a second transgenic mouse of the present invention to which the compound was not administered.

A further embodiment of the current invention is the application of the urocortin-deficient mice to the study of the physiology of the HPA axis. A method is provided for screening a compound for effects on the response of the hypothalamic-pituitary-adrenal axis to stress, comprising the steps of: a) administering the compound to a transgenic mouse of the present invention; b) placing the mouse in a stress-inducing situation; c) monitoring plasma levels of corticosterone and adrenocorticotropic hormone (ACTH) in the mouse; and d) comparing the levels to those in a transgenic mouse of the present invention not placed in the stress-inducing situation.

Yet another embodiment of the current invention relates to the use of the mice in the study the effect of urocortin on other proteins such as corticotropin releasing factor and corticotropin.

A further embodiment of the current invention is the use of urocortin-deficient mice to examine CRFR1 and CRFR2 responses unhindered by the presence of urocortin.

Examination of the urocortin null mutant mice reveals that the loss of the urocortin gene results in heightened auditory thresholds. Thus, another embodiment of the instant invention is the application of the urocortin null mutant mice to the study of molecular mechanisms involved in auditory function. So provided is a method of screening a compound for modulation of auditory function, comprising the steps of: a) administering the compound to the transgenic mouse of the present invention; b) testing the mouse for auditory function; and c) comparing auditory function of the mouse with auditory function of a second transgenic mouse of the present invention to which the compound was not administered.

In a further embodiment, the method of screening a compound for modulation of auditory function is by means of measuring auditory brainstem response (ABR) to pure tone frequencies.

In another embodiment of the invention, the urocortin gene results in heightened distortion products of otoacoustic emissions and the method of screening a compound for modulation of auditory is by means of measuring such distortion products of otoacoustic emissions.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate only preferred embodiments of the invention and therefore are not to be considered limiting in their scope.

FIG. 1A shows the genomic organization of the urocortin gene showing the deletion of the entire urocortin protein coding region. The targeting construct utilized for homologous recombination is also shown.

FIG. 1B shows the disrupted allele detected by Southern blotting analysis of tail DNAs isolated from the progeny of wildtype (+/+), heterozygote (+/−) and null mutant mice.

FIG. 1C shows the results of RNAse protection assay in urocortin wildtype (control), heterozygote and null mutant mice. No urocortin mRNA was detected in the Edinger Westphal (EW) region of null mutant mice.

FIG. 1D illustrates the fourth ventricle (4V) area of the brain of urocortin mutant mice. Immunohistochemical detection shows the absence of urocortin protein in the EW region of Ucn-deficient mice compared to urocortin wildtype mice (control).

FIG. 2A shows plasma levels of adrenocorticotropic hormone in pre-stressed and after restraint stress mice. Urocortin mutant mice showed normal stress response compared to wildtype littermates.

FIG. 2B shows plasma corticosterone levels in urocortin null mice and wildtypes littermates. Urocortin null mice exhibited similar hormonal response as wildtype controls.

FIG. 3A shows increased anxiety-like behavior in urocortin null mutant mice in the elevated plus maze (EPM). The percentage of time spent in the open arms of mutant mice was significantly less than that of wildtype controls (*: $p<0.05$; Student's t-Test).

FIG. 3B shows no difference in locomotor activity in the EPM between mutant and control animals as measured by closed arm entries and total arm entries.

FIG. 3C shows increased anxiety-like behavior in urocortin null mutant mice in the open-field test. The null mutants spent less time in the inner squares (*: $p<0.05$; Student's t-Test) than the wildtype controls.

FIG. 3D shows no difference in anxiety-like behavior in the light-dark emergence test for the two genotypes between the time spent in the light portion of the box or in the number of transitions between the light and dark portions of the box.

FIG. 4A-4B show autoradiographs of CRFR2 mRNA levels in the lateral septum in wildtype (A) and mutant (B) mice brains.

FIG. 4C shows a significant reduction of CRFR2 mRNA in the lateral septum of urocortin mutant mice (**: p<0.01) compared to the wildtype controls.

FIG. 5A illustrates the localization by immunostaining of urocortin fibers only within the inner hair cell region (IHC) of the organ of Corti. No immunostained profiles were observed crossing the tunnel nor in the outer hair cell region. (20× objective magnification).

FIG. 5B shows urocortin immunoreactive fibers within the inner spiral bundle (ISB) immediately beneath the inner hair cell (IHC). The arrows indicate numerous swellings, presumably synaptic terminals observed coursing toward the hair cell, and in close proximity to the base of the cell (63× objective magnification).

FIGS. 5C-5D show double arrows show CRFR1 and CRFR2 mRNAs respectively expressed over the region of outer hair cells (OHC) and supporting cells such as Henson's and Claudius cells (indicated by single arrows), lateral to the tunnel. Cresyl violet counterstain detected only background signal medial to the tunnel of Corti.

FIG. 6A urocortin null mutant mice demonstrate primary hearing deficits of auditory brainstem response (ABR) to pure tone frequencies. Urocortin null mutant mice display elevated thresholds to auditory stimuli. High frequency stimulation in the older mice shows no difference in auditory brainstem response between null and wildtype mice, due to the age related hearing deficits observed in the C57Bl/6 mouse strain used in creating these null mutants.

FIG. 6B shows significantly elevated distortion product otoacoustic emissions in the urocortin null mutant mice at all ages tested. No significant change was observed in the level of distortion products within a genotype pool in relation to age. The steady rise in thresholds observed with auditory brainstem response measurements with age is due to impaired outer hair cell function as well as an apparent, slight but statistically significant alteration in outer hair cell size observed in the urocortin mutant mice.

DETAILED DESCRIPTION OF THE INVENTION

Figure 1A:
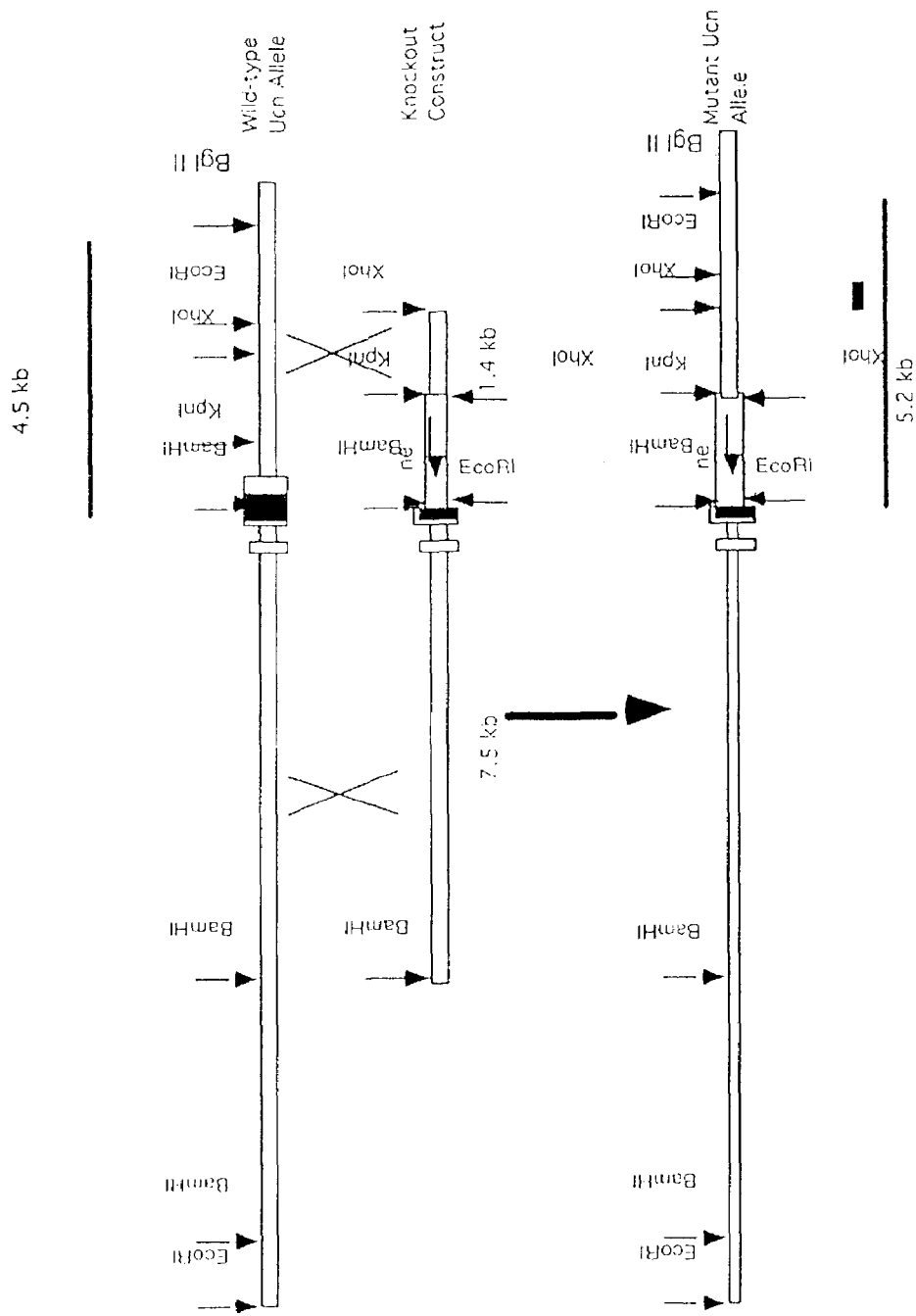
FIGS. 1A-1D show the procedure used to generate and detect Ucn-Deficient mice.
Figure 1B:
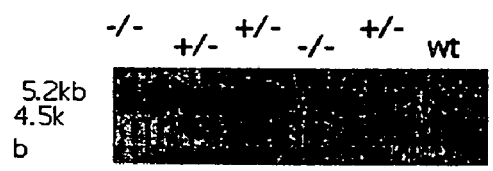
Figure 1C:
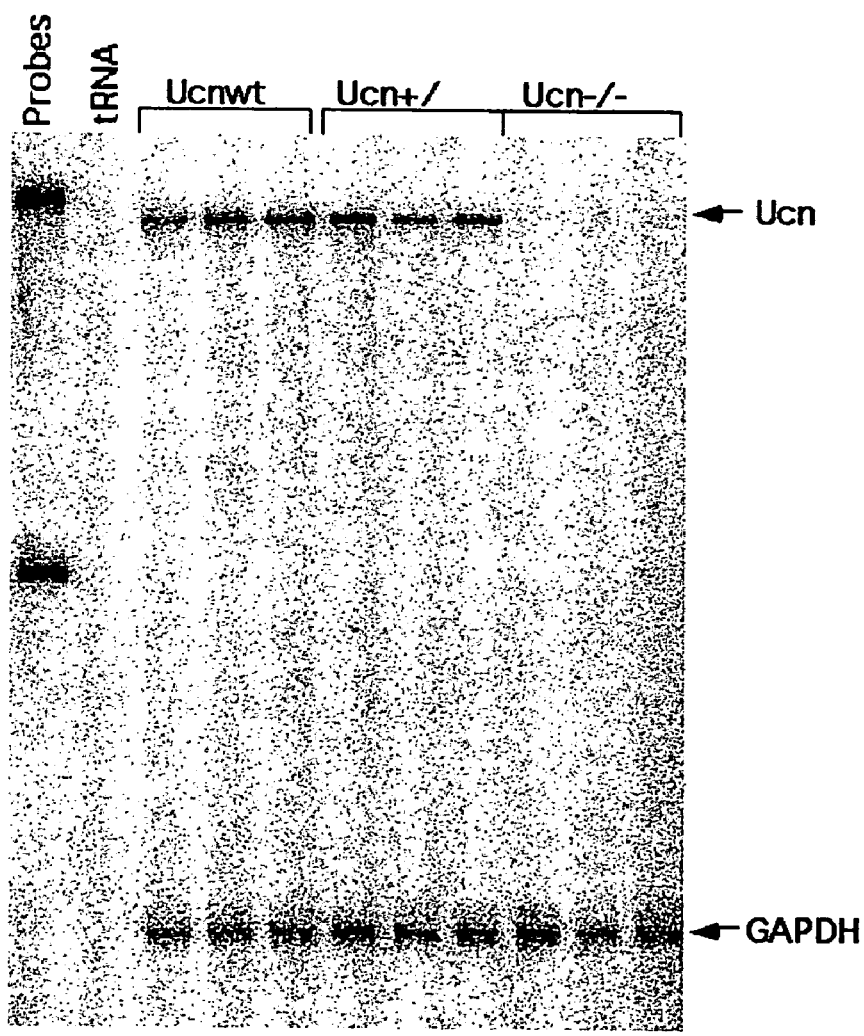
Figure 1D:
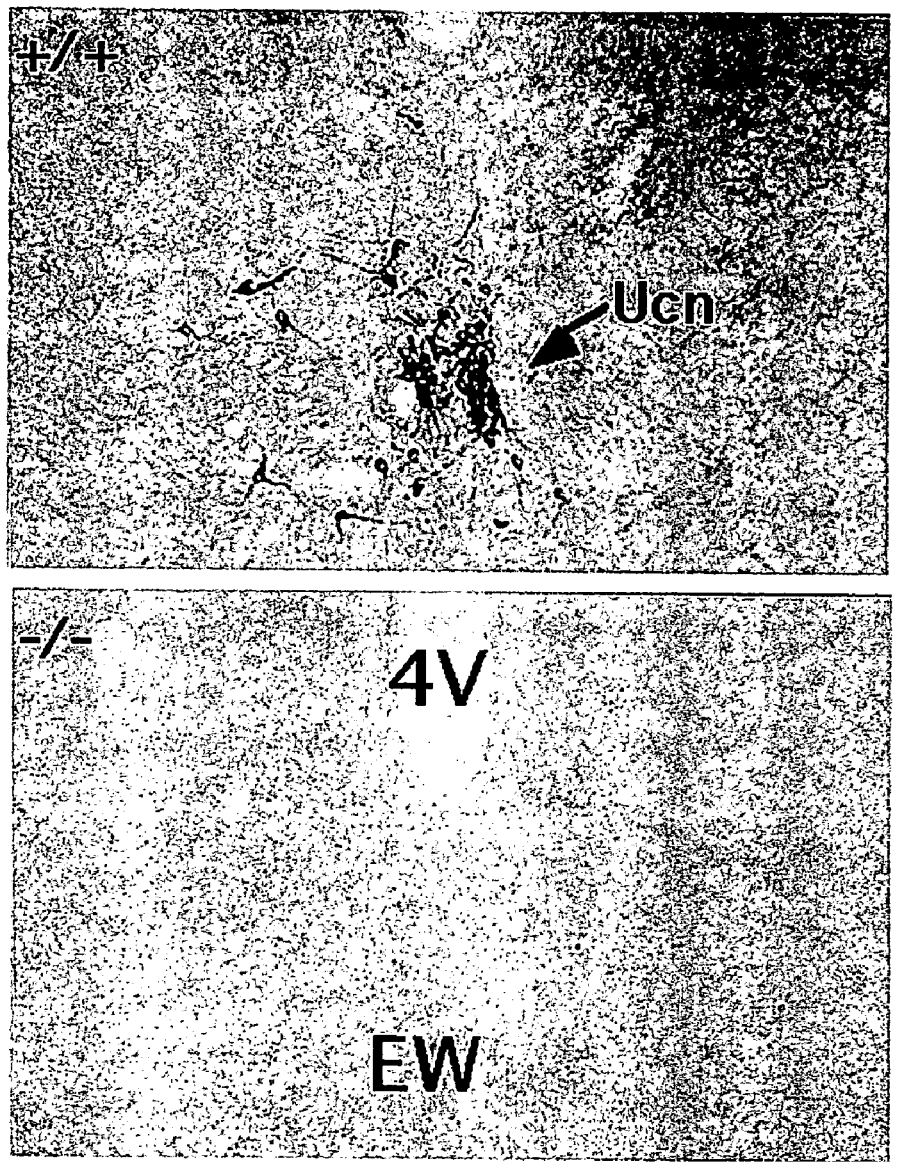

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins Eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

As used herein, the term "cDNA" shall refer to the DNA copy of the mRNA transcript of a gene.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acids described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552-59 (1969), abbreviations for amino acid residues are known in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention; the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors.

The current invention is directed to mice deficient in urocortin, which were generated to discern the developmental and physiological roles of urocortin in anxiety, HPA axis circuitry and auditory function. This has been done by deleting the DNA sequences on the urocortin gene coding for the urocortin protein. In the present invention, these sequences have been replaced with a neomycin resistance gene cassette. The mice may be either heterozygous or homozygous for the urocortin deficiency and may be crossed with mice of another strain.

The present invention is also directed to the application of the urocortin-deficient mice in the study of anxiety and auditory function, including methods of testing a compound for anxiety or hearing modulating activity.

The current invention is also directed to use of the urocortin-deficient mice in the study of the molecular physiology of the hypothalamic-pituitary-adrenal (HPA) axis. The mice can be used to test the effects of a compound on the response of the HPA axis to stress.

The current invention is also directed to the use of the transgenic mice to study the molecular functions of urocortin on corticotropin releasing factor, corticotropin releasing factor receptor 1, corticotropin releasing factor receptor 2, corticotropin and corticotropin receptors. In addition, the present invention can be used to study the relative responses and activities of CRFR1 and CRFR2 in a urocortin negative environment. The effects of CRF can be studied without the presence of urocortin.

The instant invention is also directed to the use of urocortin null mutant mice in deciphering the physiological role of urocortin in auditory function. Such auditory function is determined by recording auditory brain stem responses (ABR) and distortion products of otoacoustic emissions and comparing the readings to those observed in wildtype littermates.

The following examples are given for the purpose of illustrating various embodiments of the invention and are not meant to limit the present invention in any fashion.

EXAMPLE 1

Generation of Urocortin Deficient Mice

To generate urocortin mutant mice, a targeting vector was created in which the entire mature peptide coding region was deleted and replaced with a neomycin-resistant gene cassette (FIG. 1). The resulting plasmid was then linearized and electroporated into J1 embryonic stem (ES) cells. Neomycin resistant clones were selected and screened for the presence of the disrupted allele by Southern Blot analysis. Positive embryonic stem clones were injected into C57BL/6 blastocysts to generate chimeric mice.

Chimeric mice were crossed and first generation heterozygote mice were then maintained on both a 129/Sv and a C57Bl/6J background and crossed (brother x sister mating) with either line to generate the appropriate mice. Germline transmission of the disrupted allele was determined by Southern Blot analysis of mice tail DNAs.

EXAMPLE 2

Effects of Stress on the HPA Axis Response in Ucn-Deficient Mice

In order to examine the HPA axis response to stress, animals were subjected to physical restraint-stress for increasing lengths of time. Restraint stress was carried out in the morning about 2.5 hours after the start of the light cycle. Animals were individually restrained in ventilated 50 ml polypropylene tubes. Blood samples were collected by retro-orbital eye bleed at 2, 5 or 10 min after the stress commenced. Plasma samples were immediately centrifuged and stored at −80° C. until the assay was conducted. Plasma levels of adrenocorticotropic hormone (ACTH) and corticosterone levels were measured using an RIA kit (ACTH: Nichols Institute Diagnostics; corticosterone: ICN Biomedicals), respectively.

Figure 2A:
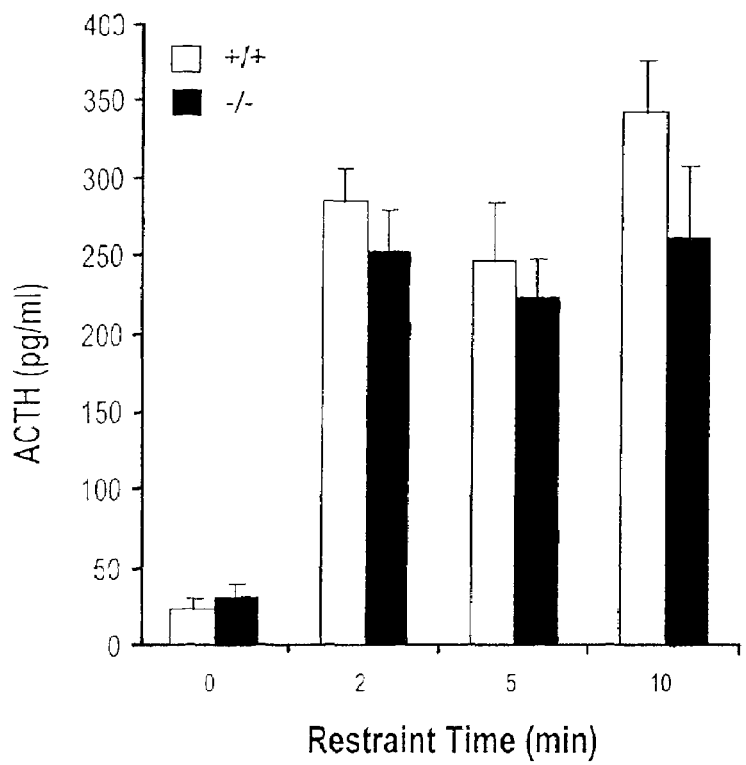
FIG. 2A-2B show the hypersensitivity of HPA axis to restraint stress in mutant animals and wildtype littermates.
Figure 2B:
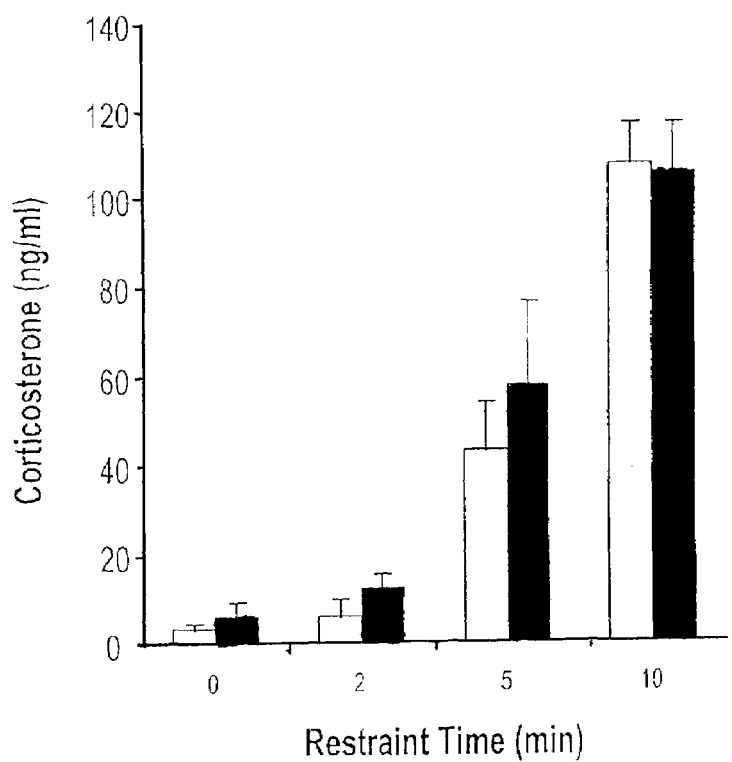

ACTH levels in the mutant mice indicated normal response to restraint stress (FIG. 2A) compared to wildtype litter mates. Similarly, corticosterone profiles in the mutant animals were similar to their wildtype counterparts (FIG. 2B). These results demonstrated that urocortin is not involved in the HPA hormone secretions in responses to acute stress or only plays a minor role in such responses.

EXAMPLE 3

Effect of Food Deprivation in Ucn-Deficient Mice

Pharmacological studies have demonstrated that urocortin and its receptors are involved in the modulation of ingestive behavior. Central administration of urocortin causes significant suppression of food intake (11), and the effects can be blocked by pre-treating animals with antisense oligonucleotides to CRFR2(39). Furthermore, it has been shown that CRFR2 deficient mice exhibit reduced food intake after overnight food deprivation compared to the wildtype controls (31). The present study determined if urocortin is essential in basal feeding behavior.

Urocortin mutants and wildtype littermates were food deprived for 24 hours with water. Pre-weighed food pellets were returned the next morning following food deprivation. Food remaining in the cage was weighed every two hours until lights off (1800 hours). Food and mice were weighed the following morning at 0900 hours for five days.

Urocortin mutants displayed normal basal food intake response as well as accumulated food intake following a 24 hour food deprivation. The results suggest that endogenous urocortin is not required for basal food intake regulation. Due to the discrepancy observed between urocortin and CRFR2 mutants in food intake, additional CRF-like peptides may interact with central CRFR2 to modulate feeding. Likely candidates of such CRF-like peptides include urocortin II and urocortin III which show high affinity to CRFR2 and suppress food intake when administered centrally into the rat brain (7-9).

EXAMPLE 4

Evaluation of Anxiety-Like Behavior in Ucn-Deficient Mice

CRFR2 mutant mice have been known to display anxiolytic-like behavior, and since urocortin binds with high affinity to CRFR2 and is thought to be its endogenous ligand, urocortin null mutant mice were analyzed for anxiety-like behavior.

Control wildtype littermates (n=7) and mutant mice (n=8) 12-16 weeks of age were evaluated using three different test paradigms: the elevated plus maze (EPM), the open field test and the light/dark box test (29).

EXAMPLE 5

Evaluation of Anxiety-Like Behavior in Ucn-Deficient Mice in Elevated Plus Maze

The behavior of urocortin null mutant and control mice was analyzed for anxiety-like behavior in an elevated plus maze. The plus maze apparatus was made of black Plexiglas and had two open arms (30×5 cm) and two enclosed arms of the same size with walls 30 cm high. It was elevated 30 cm above the ground. The arms were connected by a central square (5×5 cm) and thus the maze formed a plus sign. A 25 watt lamp placed above the apparatus provided a 6 lux light level in the open arms.

Animals were group housed and maintained under regular light/dark conditions (lights on 6:00 AM, lights off 6:00 PM), Animals were handled on alternate days one week before testing. All testing was performed during the light phase of the light-dark cycle. Mice were habituated to the experimental room conditions for 1 hour prior to the behavioral testing and the subjects were individually tested in 5-min sessions.

The mouse was placed on the center platform facing an open arm to initiate the test session. Animal behavior was observed by a camera mounted above the apparatus and viewed on a video monitor in an adjacent Behaviors scored were the number of open and closed arm entries and the amount of time spent on the various sections of the maze. Arm entries were defined as an entry of all four paws into the arm. Closed arm entries were taken as an index of locomotor activity in the plus maze. At the end of the test, the number of entries into and the time spent on the open arms were expressed as a percentage of the total number of arm entries and test duration, respectively. Results are expressed as the mean ± standard error of the mean. Behavioral parameters obtained from the EPM test were analyzed using the Student's t test.

Figure 3A:
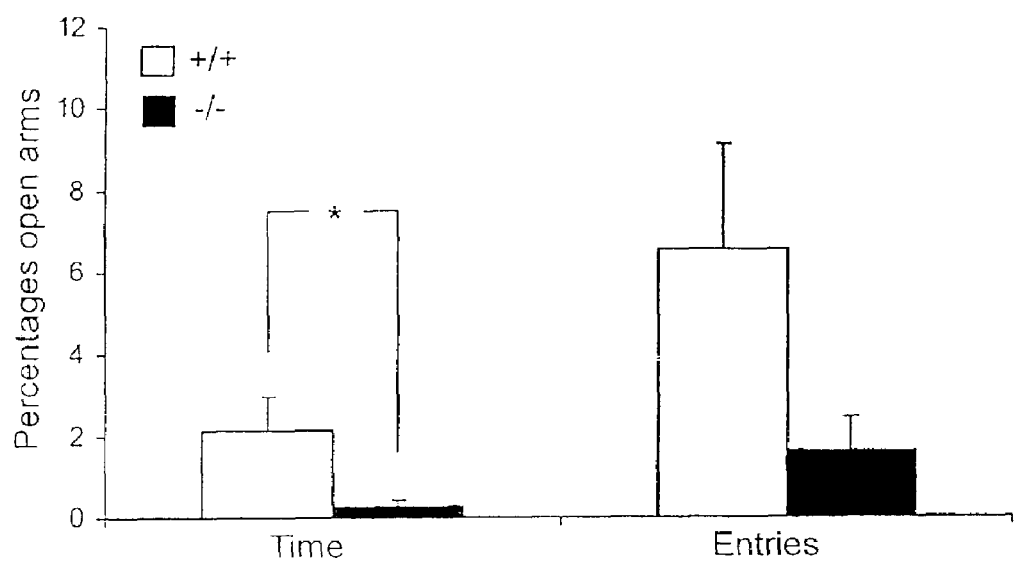
FIG. 3A-3D show increased anxiety-like behavior in urocortin null mutant mice using three different test paradigms.
Figure 3B:
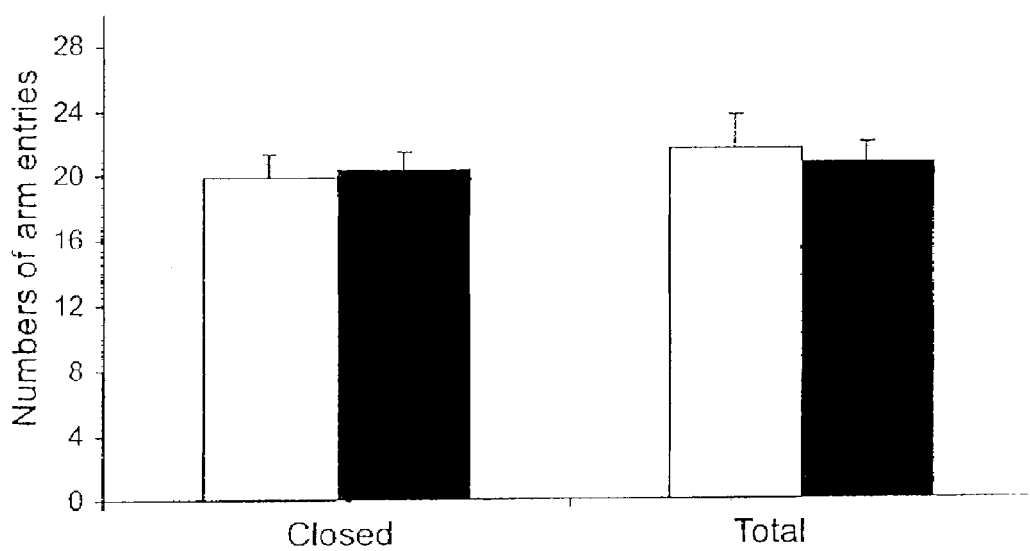
Figure 4A:
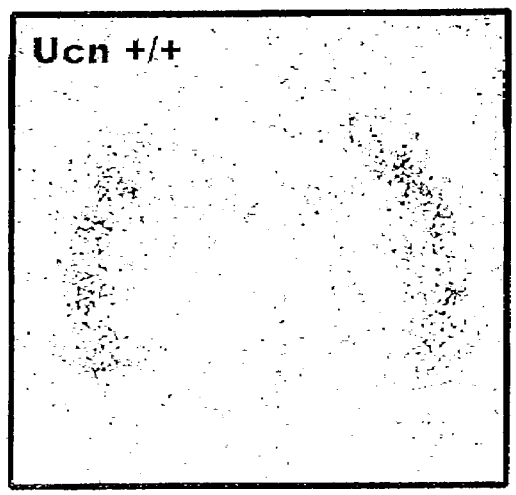
FIGS. 4A-4C show increased CRFR2 mRNA expression in the brain of urocortin mutant mice.

Urocortin null mutant mice spent significantly less time in and entered less frequently the open arms of the plus-maze apparatus than did the wild type controls (FIG. 3A). A significant effect was found for both percent entries into the open arms [t(12)=2.684; p<0.02] and percent time in the open arms [t(12)=3.524; p<0.005] (FIG. 4A). The increase in anxiety-like behavior was not due to altered locomotor activity, as overall activity in closed arm [t(12)=0.469; p=0.64] and total arm entries [t(12)=0.904; p=0.38] was not different between the two groups (FIG. 3B). These results demonstrate that urocortin null mutant mice exhibit markedly increased anxiety-like behavior.

EXAMPLE 6

Evaluation of Anxiety-Like Behavior in Ucn-Deficient Mice in the Open-Field Test The behavior of urocortin null mutant and control mice was also analyzed for anxiety-like behavior in an open-field test. The open field apparatus consisted of a white Plexiglas box (50×50×22 cm) with 16 squares (12×12 cm) painted on the floor (12 outer and 4 inner). The test was conducted during the dark phase of the light-dark cycle.

The mouse was placed in the center of the apparatus and allowed to explore the whole field for 10 minutes. The behavior was monitored and videotaped in an adjacent room. Time spent in the inner squares, ambulation (number of squares crossed), defecation, rearings and time spent grooming were quantified from the video recording. Inner square crossings were also expressed as percentage of ambulation (outer plus inner squares crossings).

Figure 3C:
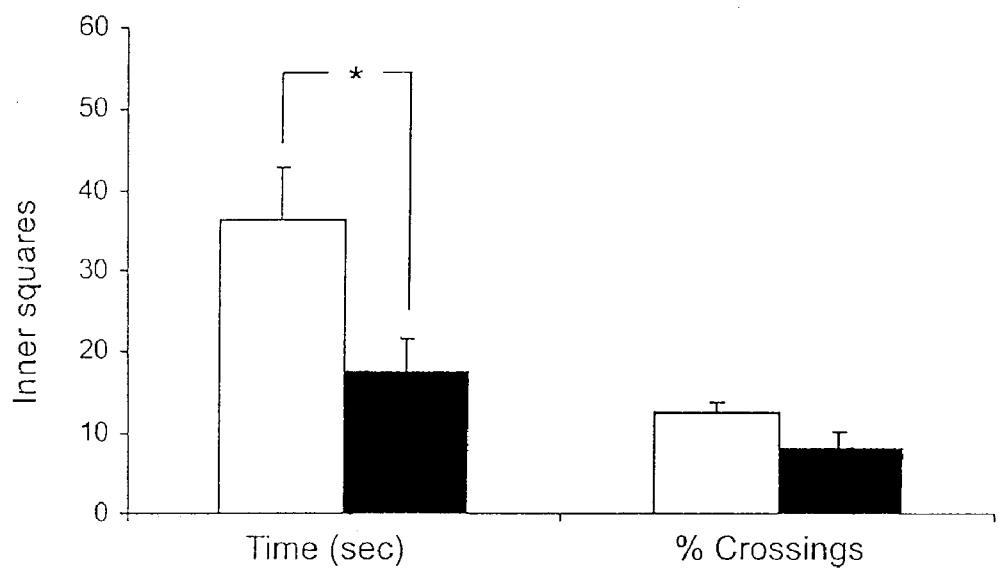

Compared to wildtype littermates, urocortin mutant mice spend less time in the inner squares (FIG. 3C). These results demonstrate that urocortin null mutant mice exhibit markedly increased anxiety-like behavior.

EXAMPLE 7

Evaluation of Anxiety-Like Behavior in CRFR2 Deficient Mice in a Light/Dark Box

The behavior of urocortin null mutant and control mice was also analyzed for anxiety-like behavior in a light/dark box. The testing apparatus consisted of a rectangular Plexiglas box divided into two compartments: one painted white (28.5 cm×27 cm) and one painted black (14.5 cm×27 cm) with a red lid covered the black compartment. The two compartments were connected by a small opening (7.5 cm×7.5 cm). Light intensity was 8 lux in the black compartment (dark side) and 400 lux in the white compartment (light side).

The mouse was placed in the center of the white compartment and allowed to explore the whole apparatus for 10 min. Testing was carried out during the dark phase of the light-dark cycle. The behavior of the mouse was also monitored and videotaped in an adjacent room. A camera mounted above the apparatus allowed for observation and recording from an adjacent room. The time spent in the light compartment and the number of transitions between the two compartments were recorded and scored from the videotapes.

Figure 3D:
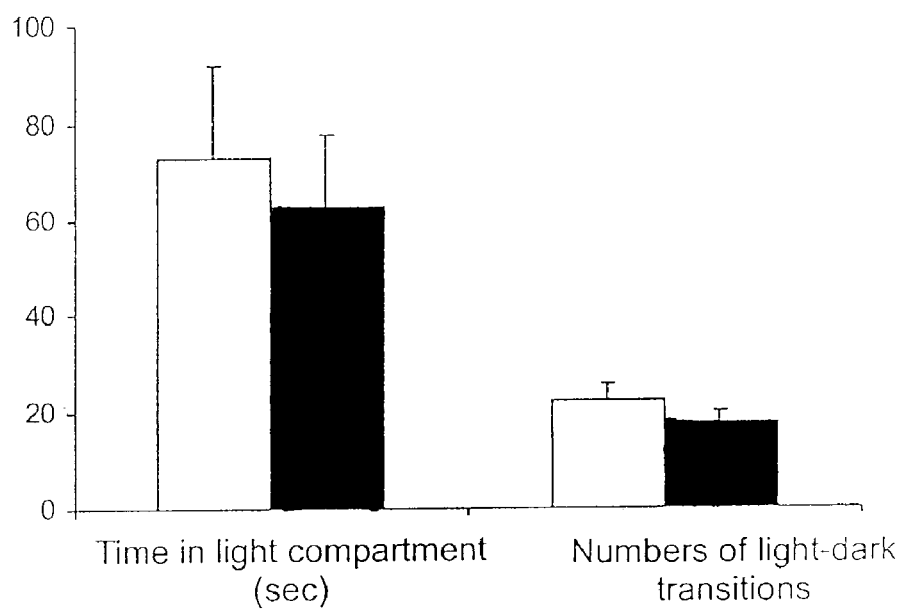

Results from the Light/Dark box demonstrated that urocortin null mutant mice spent as much time in the light portion of the box and had as many transitions between the light and dark portions of the box as control mice (FIG. 3D). No significant differences were detected between the two groups in this experiment.

EXAMPLE 8

Effect of Urocortin Deficiency on CRF, CRFR1, CRFR2 mRNA Expression

To determine if the targeted urocortin null mutation deletion resulted in a change in mRNA expression of CRF, CRFR1 or CRFR2, in situ hybridization was performed as previously described (45). Briefly, tissue sections were fixed, cryoprotected, cut on a cryostat at 10-20 µm, and mounted directly onto gelatin coated slides. Sections were hybridized overnight with $^{35}S$ antisense RNA probes overnight at 57° C. on a slide warming tray. Following incubation, slides were washed and submitted to RNase digestion (Promega) and a high stringency wash with 0.1×SSC at 65° C. for 30 minutes. Slides were coated with Amersham LM-1 emulsion, and exposed for various periods of time, up to 14 days, at 4° C. The slides were photographically processed, counter-stained, coverslipped and imaged.

Figure 4B:
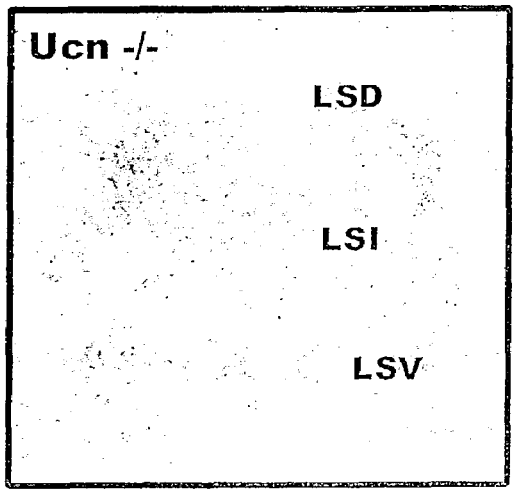
Figure 4C:
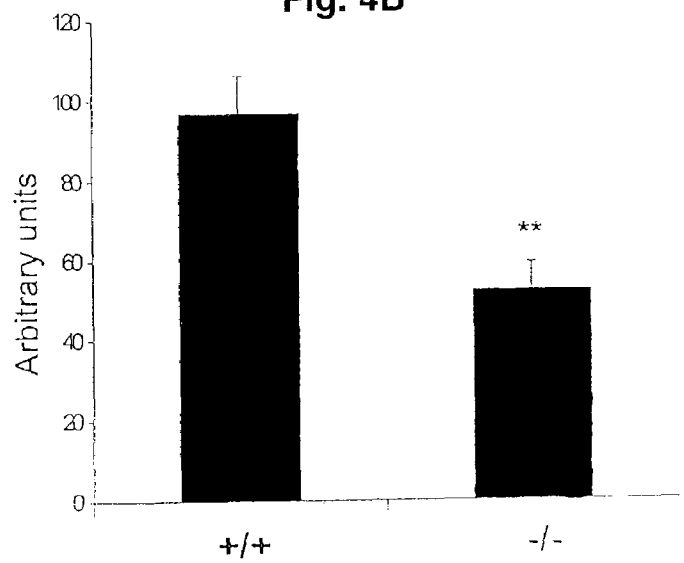

In the lateral septum, the autoradiographs show no difference in the CRF and CRFR1 mRNA levels between Ucn-deficient mutants and wildtype littermates. However, the CRFR2 mRNA levels were significantly reduced in Ucn-deficient mice compared to wildtype controls (p<0.01). (FIGS. 4A and 4B).

EXAMPLE 9

Histological Analysis of Ucn, CRFR1 and CRFR2 in the Inner Ear of Mice

To locate urocortin immunoreactive terminals and CRF receptors in the inner hair cell region of the mouse organ of Corti, mice cochleas were perfused via the round and oval windows with Zamboni fixative (4% paraformaldehyde, 15% saturated picric acid, buffered with PBS). The temporal bone was immediately isolated and immersed in the same fix for one hour at room temperature. The tissue was then rinsed in PBS, and decalcified overnight at room temperature using 8% EDTA in PBS. The membranous labyrinth was isolated, and individual turns were cut from the spiral. Rabbit anti-urocortin primary antibodies used for immunostaining.

Figure 5A:
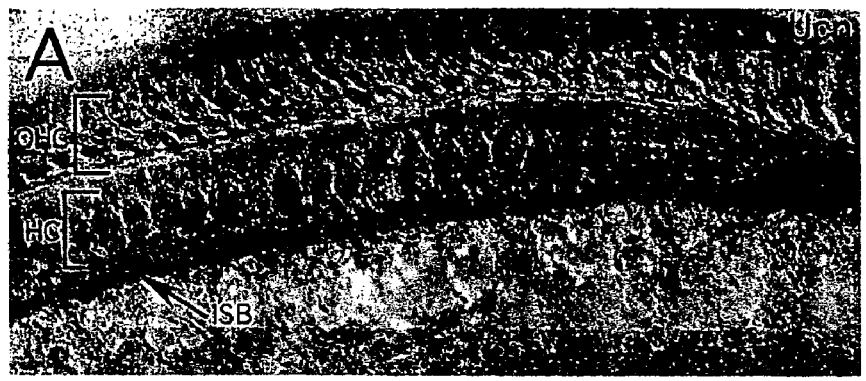
FIG. 5A-5D show immunostaining of an extensive network of urocortin immunoreactive terminals and CRF receptors in the inner hair cell region of the mouse organ of Corti.
Figure 5B:
Figure 5C:
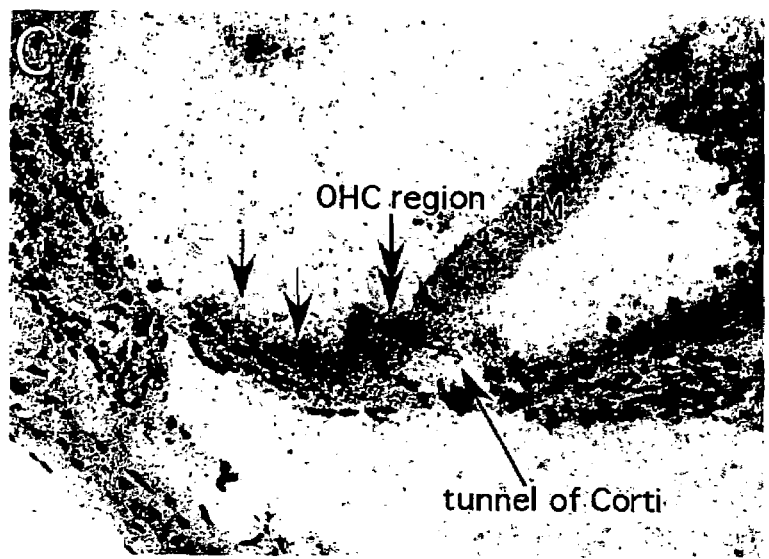
Figure 5D:
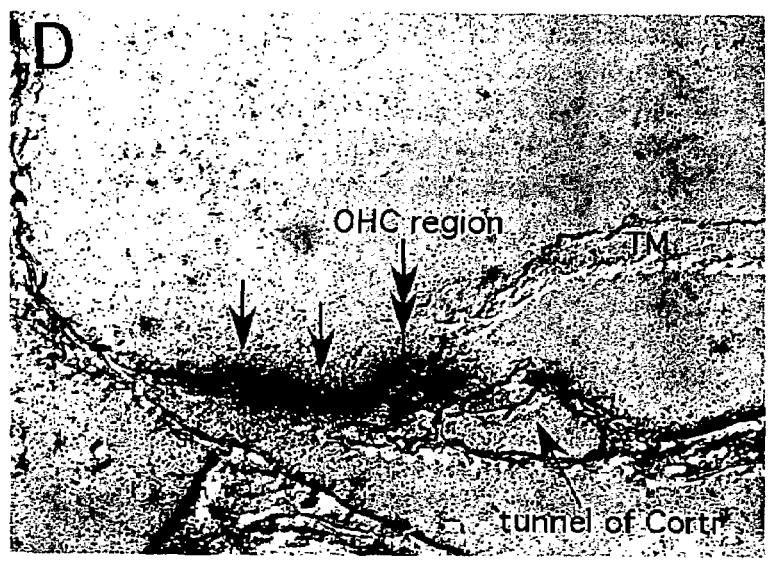

Urocortin fibers were immunolocalized only within the inner hair cell region (IHC) of the organ of Corti but not in the tunnel or in the outer hair cell region (FIG. 5A). Urocortin immunoreactive fibers were also detected within the inner spiral bundle (ISB) immediately beneath the inner hair cell (IHC) (FIG. 5B).

CRFR1 and CRFR2 mRNAs (double arrows) were respectively expressed over the region of outer hair cells (OHC) and supporting cells such as Henson's and Claudius cells (single arrows), lateral to the tunnel. Medial to the tunnel of Corti, cresyl violet counterstain detected only background signal but not CRFR1 and DIC optics did not show and expression of CRFR2.

EXAMPLE 10

Auditory System Impairment in Ucn-Deficient Mice

Mice cochleas were isolated, perfused, decalcified, and finally embedded either in plastic or paraffin. Plastic semi-thin sections 2 µm thick or paraffin sections 10 µm thick were cut through the entire cochlea, and mid-modiolar sections were analyzed. Middle row outer hair cells from the middle turn were measured in six mice (three mutants and three wildtypes). In total, 50 distinct hair cells from each genotype were measured. Statistical analysis was carried out only after all data were collected.

The organ of Corti appeared grossly normal in its overall morphology. However, measurements of outer hair cell length revealed a small, but consistent and statistically significant difference in the size in the mutant mice compared to wildtype littermates (wildtype,13.8±0.6 µm; mutants, 12.4±0.3 µm; p<0.05).

Anti-synaptophysin antibodies were used to reveal all synaptic terminals within the organ of Corti. No changes were observed in the number of terminals contacting the outer hair cells or present in the inner spiral bundle compared to wildtype littermate controls at 3 months of age (data not shown). Such results demonstrate that urocortin is not essential for the anatomical integrity of the olivocochlear system.

EXAMPLE 11

Auditory Function in Ucn-Deficient Mice

Auditory testing was performed essentially where mice were anesthetized with xylazine (20 mg/kg i.p.) and ketamine (100 mg/kg i.p.). For auditory brainstem responses, needle electrodes were inserted at vertex and pinna, with a ground near the tail. Stimuli were 5-msec tone pips delivered at 35/sec. At each test frequency, the sound pressure level was varied in 5-dB steps from 5 dB up to at least 20 dB above "threshold", as defined by visual inspection of response waveforms.

At both 3 and 6 months of age, urocortin null mice display elevated thresholds to auditory stimuli measured by auditory brainstem response (ABR) to pure tone frequencies. For older mice, there is no difference between null and wild type mice in relation to high frequency stimulation due to age related hearing deficits observed in the C57Bl/6 mouse strain used in creating these null mutants. These results show that outer hair cell function is impaired in urocortin-deficient mice.

EXAMPLE 12

Auditory Function in Ucn-Deficient Mice

Similar to the method of Example 11, distortion product otoacoustic emissions were measured with an ER-10C system. The distortion product otoacoustic emissions (DPOAE) assay is a non-invasive method to test the functional state of the outer hair cell population and requires these cells to be intact to generate the emissions (35, 36). Distortion products are propagated from the inner ear to the external ear canal via the middle ear ossicles and eardrum, and can be measured in the sound pressure waveform within the canal with the use of sensitive microphones (37).

Two primary tones ($f_2$:$f_1$=1.2) were presented with $f_2$ level 10 dB<$f_1$. A fast Fourier transform was computed, and sound pressures at $f_1$, $f_2$ and $2f_1$-$f_2$ extracted after spectral averaging from 5 serial waveform traces. The iso-response contours for distortion product otoacoustic emissions were interpolated from the amplitude-vs.-level functions: the criterion response was a $2f_1$-$f_2$ DPOAE of 0 dB SPL.

For all ages tested, urocortin null mutants showed significantly elevated distortion product otoacoustic emissions. Within a genotype pool in relation to age, no significant change was observed in the level of distortion products. Therefore, the increase in thresholds observed with the ABR measurements with age in Example 11 cannot be simply explained by impaired outer hair cell function. The observed rise in distortion product thresholds implicates a correlation with a slight but statistically significant alteration in OHC size observed in the urocortin null mice (Example 10).

EXAMPLE 13

Effects of Urocortin Gene Deletion on Stress and Auditory Function

The results presented here suggest that urocortin null mutant mice display normal hormonal responses to acute stress. Thus, endogenous urocortin cannot be involved in the regulation of HPA hormone secretions in response to stress or may only play a minor role in HPA stress responses. The results reinforce findings in an earlier study where anti-urocortin failed to block stress induced ACTH and corticosterone secretion (38).

In the present study, urocortin-deficient mice displayed basal food intake response as well as accumulated food intake following a 24-hour food deprivation that were comparable to wildtype littermates, indicating that endogenous urocortin is not involved in basal food intake regulation. These findings are in contrast to those previously obtained for CRFR2-deficient mice, which suggest that other urocortin-like peptides like urocortin II and III may possibly play a role in interacting with CRFR2 to regulate basal food metabolism.

In anxiety behavior tests, urocortin mutant mice displayed increased anxiety-like behavior in the EPM. Interestingly, since urocortin mutants and wildtype littermates expressed similar levels of CRF and CRFR1 mRNAs, the anxiety-like behavior observed could not be due to the overexpression of CRF or CRFR1, but may possibly be due to the corresponding and significant reduction of CRFR2 expression in the urocortin-deficient mice. These findings are consistent with previous studies of CRFR2-deficient mice, which also exhibited anxiety-like behavior in the EPM. Together with current findings, urocortin neurons in the Edinger-Westphal nucleus (10) may well modulate anxiety through CRFR2 in the lateral septum to regulate exploratory behavior in aversive environments.

In the open filed test, urocortin-deficient mice again exhibited anxiety-like behavior, spending less time in the inner squares than do wildtype mice. However, urocortin-mutant mice showed behavior comparable to wildtype mice in the light/dark box. Profiles from the three test paradigms show that urocortin-deficient mice demonstrates heightened emotionality relating to exploration of aversive environments but not neophobia.

With respect to the auditory system, urocortin mutant mice present with a normal and intact gross organ of Corti. Anti-synaptophysin antibodies revealed no changes observed in the number of synaptic terminals contacting the outer hair cells or present in the inner spiral bundle of urocortin mutants compared to wildtype littermate controls at 3 months of age (data not shown). Thus, urocortin is not essential for the anatomical integrity of the olivocochlear cholinergic system.

Figure 6A:
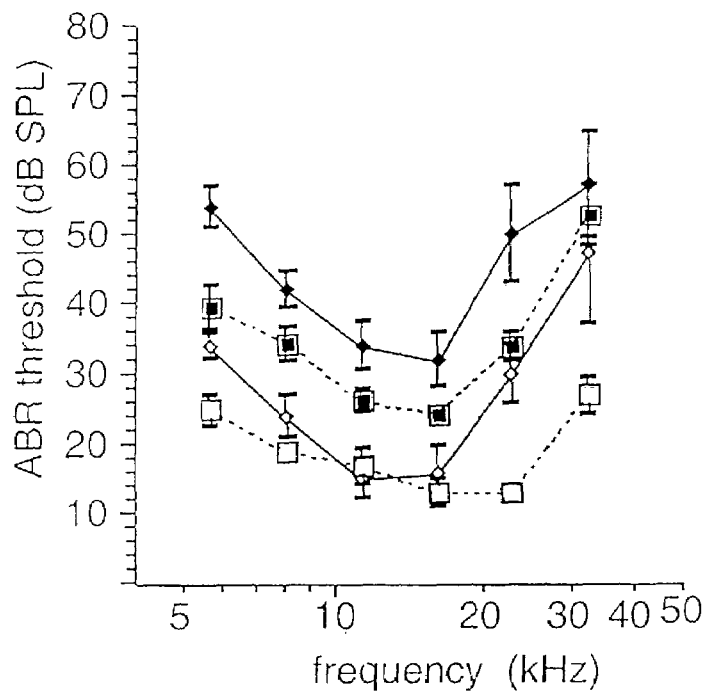
FIGS. 6A-6B show hearing impairment in urocortin mutant mice.

In the test for auditory function, however, three and six month old urocortin null mice displayed heightened auditory thresholds examined by recording the auditory brainstem response (ABR) compared to wildtype controls. At frequencies of 5.6 kHz, 8.0 kHz, 11.3 kHz, 16.0 kHz, 22.6 kHz, and 32.0 kHz urocortin mutant mice consistently displayed an elevated threshold (FIG. 6A). Respectively, three months old mutant mice displayed mean differences of 14 dB at 5.6 kHz, 15 dB at 8.0 kHz, 9 dB at 11.3 kHz, 11 dB at 16.0 kHz, 21 dB at 22.6 kHz, and 26 dB at 32.0 kHz compared to wildtype littermate controls (all p<0.05), suggesting that the congenital lack of urocortin expression results in a significant auditory threshold shift over all frequencies tested.

At six months, greater differences were detected between urocortin null mutants and their littermate controls. The mean differences observed for each of the tested frequencies (in the same order as reported above) was 20 dB, 18 dB, 19 dB, 16 dB, 20 dB, and 10 dB. All threshold changes were significantly different except for the 32.0 kHz difference. At 32.0 kHz, hearing loss observed was most likely attributable to older C57Bl/6 mice (34).

Figure 6B:
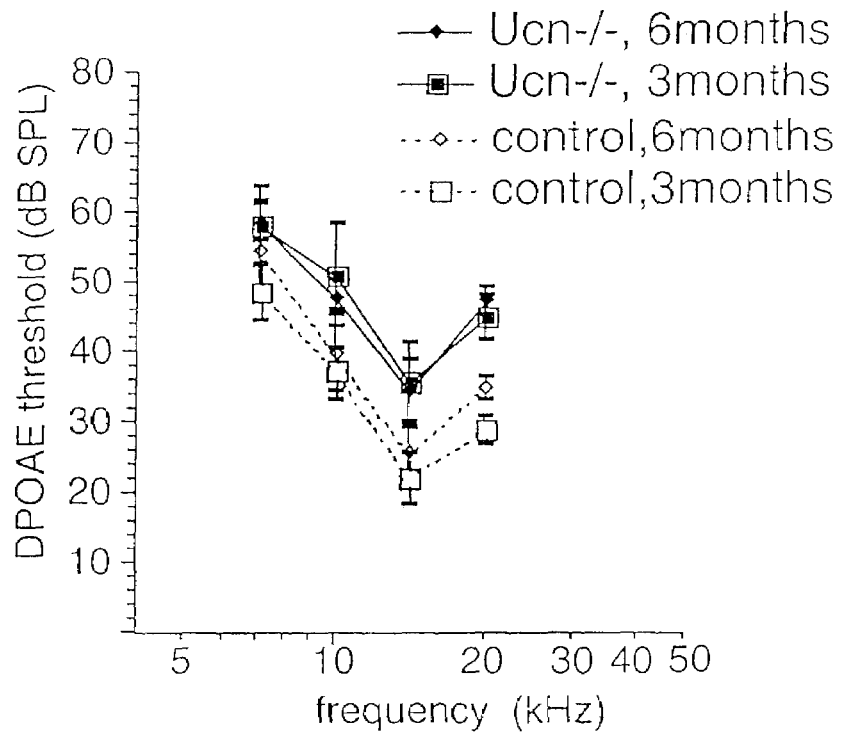

In another non-invasive auditory test, distortion product otoacoustic emissions were observed in the urocortin mutant mice, indicating a functional outer hair cell population (FIG. 6B). However, a statistical examination (two way ANOVA) of the primary level necessary to generate a distortion product otoacoustic emission amplitude of 0 dB revealed highly significant differences between the urocortin mutant and littermate controls (p<0.0001), but not within the same genotype across ages. However, there is no age component in performance differences observed between mice of the same genotype.

Given that the observed increase in auditory thresholds, and the fact that there is no change in distortion product otoacoustic emission activity over age while there is a consistent elevation of the thresholds with increasing age, suggests that much of the threshold changes observed in the urocortin null mouse stem from the lack of urocortin activity at the lateral olivocochlear synapse.

Also given that urocortin is expressed only in the lateral olivocochlear system, and only under inner hair cells, the findings indicate that the lateral olivocochlear system is able to influence the outer hair cell region in a paracrine fashion during development, and seems to play a role in establishing mature hearing properties.

The following references were cited herein:
1. Vale, et al. *Science* 213, 1394-1397 (1981).
2. Chadwick, D. J., Marsh, J. & Ackrill, K. *Corticotropin-Releasing Factor*, (John Wiley, London, 1993).
3. Ledaris, et al. *Science* 218(1982).
4. Lederis, K. et al. *Proc West Pharmacol Soc* 25, 223-7 (1982).
5. Montecucchi, P. C. & Henschen, *Int. J. Peptide Protein Res.* 18(1981).
6. Vaughan, J. et al. *Nature* 378, 287-292 (1995).
7. Reyes, T. M. et al. *Proc Natl Acad Sci USA* 98, 2843-2848. (2001).
8. Lewis, K. et al. Identification of urocortin III, an additional member of the corticotropin-releasing factor (CRF) family with high affinity for the CRF2 receptor. *Proc Natl Acad Sci USA* 98, 7570-5. (2001).
9. Hsu, S. Y. & Hsueh, A. J. Human stresscopin and stresscopin-related peptide are selective ligands for the type 2 corticotropin-releasing hormone receptor. *Nat Med* 7, 605-11. (2001).
10. Bittencourt, J. C. et al. Urocortin expression in rat brain: evidence against a pervasive relationship of urocortin-containing projections with targets bearing type 2 CRF receptors. *J Comp Neurol* 415, 285-312. (1999).
11. Spina, M. et al. Appetite-suppressing effects of urocortin, a CRF-related neuropeptide. *Science* 273, 1561-4. (1996).
12. Kihara, N. et al. Effects of central and peripheral urocortin on fed and fasted gastroduodenal motor activity in conscious rats. *Am J Physiol Gastrointest Liver Physiol* 280, G406-19. (2001).
13. Moreau, et al. Urocortin, a novel neuropeptide with anxiogenic-like properties. *Neuroreport* 8, 1697-701. (1997).
14. Slawecki, et al. Neurophysiological effects of intracerebroventricular administration of urocortin. *Peptides* 20, 211-8 (1999).
15. Warr, W. B. Organization of olivocochlear efferent systems in mammals. in *Mammalian Auditory Pathway: Neuroanatomy*, Vol. 1 (ed. Webster, D.) 410-448 (Springer, N.Y., 1992).
16. Vetter, et al. Distribution and dendritic features of three groups of rat olivocochlear neurons. A study with two retrograde cholera toxin tracers. *Anat Embryol (Berl)* 185, 1-16 (1992).
17. Hashimoto, et al. *Acta Otolaryngol (Stockh)* 109, 228-34 (1990).
18. Liberman, M. Efferent synapses in the inner hair cell area of the cat cochlea: an electron microscopic study of serial sections. *Hear Res* 3, 189-204 (1980).
19. Vetter, D. E., Adams, J. C. & Mugnaini, E. Chemically distinct rat olivocochlear neurons. *Synapse* 7, 21-43 (1991).
20. Hoffman, et al. High-performance liquid chromatographic identification of enkephalin-like peptides in the cochlea. *Hear Res* 9, 71-8 (1983).
21. Altschuler, et al. Colocalization of enkephalin-like and choline acetyltransferase-like immunoreactivities in olivocochlear neurons of the guinea pig. *J Histochem Cytochem* 32, 83-43 (1984).
22. Abou-Madi, et al. Coexistence of putative neuroactive substances in lateral olivocochlear neurons of rat and guinea pig. *Hear Res* 30, 135-46 (1987).
23. Hoffman, et al. Proenkephalin and prodynorphin related neuropeptides in the cochlea. *Hear Res* 17, 47-50 (1985).
24. Altschuler, et al. Localization of dynorphin B-like and alpha-neoendorphin-like immunoreactivities in the guinea pig organ of Corti. *Hear Res* 17, 249-58 (1985).
25. Adams, et al. A possible neurotransmitter role for CGRP in a hair-cell sensory organ. *Brain Res* 419, 347-51. (1987).
26. Bailey, G. P. & Sewell, W. F. Calcitonin gene-related peptide suppresses hair cell responses to mechanical stimulation in the Xenopus lateral line organ. *J Neurosci* 20, 5163-9. (2000).
27. Sewell, et al., Effects of calcitonin gene-related peptide and efferent nerve stimulation on afferent transmission in the lateral line organ. *J Neurophysiol* 65, 1158-69. (1991).
28. Spina, M. G. Time-dependent induction of anxiogenic-like effects after central infucsion of urocortin or corticotropin-releasing factor in the rat. *Psychopharmacology (Berl)* in press(2002).
29. Smith, G. W. et al. Corticotropin releasing factor receptor 1-deficient mice display decreased anxiety, impaired stress response, and aberrant neuroendocrine development. *Neuron* 20, 1093-102. (1998).
30. Timpl, P. et al. Impaired stress response and reduced anxiety in mice lacking a functional corticotropin-releasing hormone receptor 1 [10ee comments]. *Nat Genet* 19, 162-6 (1998).
31. Bale, T. L. et al. Mice deficient for corticotropin-releasing hormone receptor-2 display anxiety-like behaviour and are hypersensitive to stress. *Nat Genet* 24, 410-4. (2000).
32. Coste, S. C. et al. Abnormal adaptations to stress and impaired cardiovascular function in mice lacking corticotropin-releasing hormone receptor-2. *Nat Genet* 24, 403-9. (2000).
33. Kishimoto, T. et al. Deletion of crhr2 reveals an anxiolytic role for corticotropin-releasing hormone receptor-2. *Nat Genet* 24, 415-9 (2000).
34. Zheng, et al. Assessment of hearing in 80 inbred strains of mice by ABR threshold analyses. *Hearing Res.* 130, 94-107 (1999).

35. Ruggero, et al. Basilar membrane responses to two-tone and broadband stimuli. *Philos Trans R Soc Lond Biol* 336, 307-14; discussion 314-5 (1992).
36. Ruggero, M. A. Responses to sound of the basilar membrane of the mammalian cochlea [published erratum appears in Curr Opin Neurobiol 1992 Oct.;2(5):690]. *Curr Opin Neurobiol* 2, 449-56 (1992).
37. Probst, et al., A review of otoacoustic emissions. *J Acoust Soc Am* 89, 2027-67 (1991).
38. Turnbull, et al. Urocortin is not a significant regulator of intermittent electrofootshock-induced adrenocorticotropin secretion in the intact male rat. *Endocrinology* 140, 71-8. (1999).
39. Smagin, et al. The role of CRH in behavioral responses to stress. *Peptides* 22, 713-24. (2001).
40. Kozicz, T., Yanaihara, H. & Arimura, A. Distribution of urocortin-like immunoreactivity in the central nervous system of the rat. *J Comp Neurol* 391, 1-10. (1998).
41. Skelton, et al. Chronic administration of the triazolobenzodiazepine alprazolam produces opposite effects on corticotropin-releasing factor and urocortin neuronal systems. *J Neurosci* 20, 1240-8. (2000).
42. Eybalin, M. Neurotransmitters and neuromodulators of the mammalian cochlea. *Physiol Rev* 73, 309-73 (1993).
43. Vetter, D. E. et al. Role of a9 nicotinic ACh receptor subunits in the development and function of cochlear efferent innervation. *Neuron* 23, 93-103 (1999).
44. Walsh, et al. Long-term effects of sectioning the olivocochlear bundle in neonatal cats. *J. Neurosci* 18, 3859-3869 (1998).
45. Elgoyhen, et al. Alpha 9: an acetylcholine receptor with novel pharmacological properties expressed in rat cochlear hair cells. *Cell* 79, 705-15 (1994).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A transgenic mouse whose genome comprises a homozygous disruption of the urocortin gene such that said mouse does not express urocortin protein, wherein said mouse exhibits increased anxiety-like behavior and impaired auditory function compared to a wild-type mouse.

2. The transgenic mouse of claim 1, wherein the disruption comprises a deletion of said urocortin gene.

3. The transgenic mouse of claim 2, wherein a neomycin-resistance gene cassette has been inserted in place of said deleted urocortin gene.

4. The progeny of a mating between a mouse of claim 3 and a mouse of another strain, wherein the progeny has a homozygous disruption in the urocortin gene, wherein said progeny exhibits increased anxiety-like behavior and impaired auditory function compared to a wild-type mouse.

* * * * *